(12) United States Patent
Daigle

(10) Patent No.: US 9,384,530 B2
(45) Date of Patent: Jul. 5, 2016

(54) ENHANCED ULTRASOUND IMAGE FORMATION USING QUALIFIED REGIONS OF OVERLAPPING TRANSMIT BEAMS

(75) Inventor: Ronald Elvin Daigle, Redmond, WA (US)

(73) Assignee: Verasonics, Inc., Redmond, WA (US)

( * ) Notice: Subject to any disclaimer, the term of this patent is extended or adjusted under 35 U.S.C. 154(b) by 66 days.

(21) Appl. No.: 14/115,042

(22) PCT Filed: May 2, 2012

(86) PCT No.: PCT/US2012/036155
§ 371 (c)(1),
(2), (4) Date: Jan. 27, 2014

(87) PCT Pub. No.: WO2012/151300
PCT Pub. Date: Nov. 8, 2012

(65) Prior Publication Data
US 2014/0140600 A1  May 22, 2014

Related U.S. Application Data

(60) Provisional application No. 61/481,476, filed on May 2, 2011.

(51) Int. Cl.
| | |
|---|---|
| G06T 5/00 | (2006.01) |
| A61B 8/00 | (2006.01) |
| A61B 8/08 | (2006.01) |
| G01S 7/52 | (2006.01) |
| G01S 15/89 | (2006.01) |

(52) U.S. Cl.
CPC .............. *G06T 5/001* (2013.01); *A61B 8/4488* (2013.01); *A61B 8/5207* (2013.01); *G01S 7/5202* (2013.01); *G01S 7/52033* (2013.01); *G01S 7/52046* (2013.01); *G01S 7/52085* (2013.01); *G01S 15/8927* (2013.01); *G01S 15/8979* (2013.01); *G01S 15/8984* (2013.01)

(58) Field of Classification Search
None
See application file for complete search history.

(56) References Cited

U.S. PATENT DOCUMENTS 4,159,462 A * 6/1979 Rocha et al. ............... 367/97
5,908,391 A * 6/1999 Muzilla et al. ............ 600/454
(Continued)

FOREIGN PATENT DOCUMENTS

| WO | 2006/113445 A1 | 10/2006 |
| WO | 2007/133882 A2 | 11/2007 |
| WO | 2009/158399 A1 | 12/2009 |

*Primary Examiner* — Jon Chang
(74) *Attorney, Agent, or Firm* — Seed IP Law Group PLLC

(57) ABSTRACT

A method and related system for improving resolution and frame rate of ultrasound images that includes specifying individual element transmit characteristics for each transmit beam in a set of transmit beams; determining various attributes of the transmit beams at field points in the field of view; using one or more of the attributes to determine if received ultrasound echo signals contributed by each transmit beam are qualified for use in image formation, and if so, how the signal should be processed; storing the determined information for each field point for repeated use with each new image frame; using the stored information to select and process subsequent received echo signals for each field point to produce an image parameter at the field point for each qualified echo signal; and combining multiple image parameters from overlapping transmit beams for a field point to produce a final image parameter that constitutes the field point value for the image frame.

26 Claims, 9 Drawing Sheets

Four overlapping transmit beams, showing field points in overlapped regions where three or four received echo signals can be combined for image formation.

(56) References Cited

U.S. PATENT DOCUMENTS

| | | | |
|---|---|---|---|
| 6,056,693 A * | 5/2000 | Haider | 600/443 |
| 6,514,205 B1 | 2/2003 | Lee et al. | |
| 2003/0125628 A1 * | 7/2003 | Song et al. | 600/447 |
| 2007/0081711 A1 | 4/2007 | Kim et al. | |
| 2007/0238954 A1 | 10/2007 | White et al. | |
| 2009/0069692 A1 * | 3/2009 | Cooley et al. | 600/459 |
| 2009/0069693 A1 * | 3/2009 | Burcher et al. | 600/459 |
| 2009/0129651 A1 | 5/2009 | Zagzebski et al. | |
| 2009/0306512 A1 * | 12/2009 | Loftman et al. | 600/447 |
| 2009/0326379 A1 * | 12/2009 | Daigle et al. | 600/453 |

* cited by examiner

Transmit waveforms at different field points, showing a secondary peak at the off axis field point. The waveform's time origin is at the first point of contact of the transmit beam pulse with the field point.

Four overlapping transmit beams, showing field points in overlapped regions where three or four received echo signals can be combined for image formation.

ENHANCED ULTRASOUND IMAGE FORMATION USING QUALIFIED REGIONS OF OVERLAPPING TRANSMIT BEAMS

CROSS-REFERENCE TO RELATED APPLICATIONS

This application claims the benefit under 35 U.S.C. §119 (e) of U.S. Provisional Patent Application No. 61/481,476 filed 2 May 2011, where this provisional application is incorporated herein by reference in its entirety.

BACKGROUND

1. Technical Field

The present disclosure pertains to ultrasound imaging and, more particularly, to a method and system for determining and utilizing image field point characteristics for image formation processing.

2. Description of the Related Art

Ultrasonic imaging utilizes high frequency sound waves to visualize the interior of objects. For example, acoustic sensing devices, such as ultrasonic inspection equipment, are used in inspecting the interiors of a variety of objects, including the human body, the area around a weld, and manufactured products such as wood-based panels. While the present disclosure is described in the context of tissue imaging, such as medical sonography, it will have application outside this field.

Medical ultrasound Imaging has developed into an effective tool for diagnosing a wide variety of disease states and conditions. The market for ultrasound equipment has seen steady growth over the years, fueled by improvements in image quality and the capability to differentiate various types of tissue. Ultrasound imaging has always required extensive signal and image processing methods, especially for array systems employing as many as 128 or more transducer elements, each with unique signal processing requirements. The last decade has seen a transition to the improved accuracy and flexibility of digital signal processing in almost all systems except for those at the lowest tiers of the market. This transition has provided the potential for improved methods of image formation that can utilize more of the information in the transmitted sound waves and returned ultrasound echo signals.

Commercial ultrasound systems typically utilize focused transmit beams for image formation. A two dimensional image field is typically insonified with a set of transmit beams that are spaced uniformly across the width of the field, each focused at a depth in the field where the best image resolution is desired. The returning ultrasound echoes from each sequential transmit beam are received and processed to obtain one of more lines of image data, where the lines correspond to the axis of each transmit beam in the set. The multiple image data lines are then interpolated into a pixel array to produce an image.

The foregoing method is illustrated in FIG. 1. A typical sequential line scan 30 might comprise 128 transmit beams 32, resulting in 128 image lines 34 that are then interpolated into pixels 36 for display. In general, the transmit beams 32 are considerably broader than the reconstructed image line 34, especially at depths other than the focal depth of the transmit beam. This results in the lateral resolution varying with depth, with the sharpest resolution obtained at the transmit focal zone as shown in FIG. 1. Only the field points along the axis of the beam are used for reconstructing the image parameters, resulting in a set of image lines 34 equal to the number of transmit beams 32 used in the scan. Because this set of image lines 34 is generally sparsely spaced relative to the spacing of pixels 36 in the display 38, the points in the image lines 34 must be interpolated for each pixel 36 in the display.

Modern commercial systems attempt to improve lateral resolution over a larger depth of field by utilizing multiple transmissions at each sequential scan position across the width of the field. At each position, the multiple transmit beams utilize different focal zones spread over the depth of interest. The image line data from each zone are combined, providing a larger effective depth of field. This technique improves lateral resolution at the cost of increased acquisition time, or lower frame rate. The time to produce a full image frame is the sum of the times needed for acquiring echo signals from each of the individual transmit beams, which is generally limited by the speed of sound and the maximum depth of interest in the medium being imaged. The more transmit beams utilized for each image frame, the longer it takes to acquire the image frame and the slower the frame rate.

Because frame rate is an important factor in many ultrasound applications, another technique is often utilized to reduce image acquisition times. The transmit beam is weakly focused so that multiple receive lines can be reconstructed in each beam, thus allowing the transmit beams to be spaced further apart over the width of the field, and reducing the total number of transmit beams needed to cover the image field. While this technique speeds up image acquisitions and can recover some of the frame rate lost to the use of multiple focal zones, lateral resolution is typically degraded due to the broadening of each transmit beam.

BRIEF SUMMARY

In accordance with one aspect of the present disclosure a method and system for improving both the resolution and frame rate of ultrasound images obtained from a multi-element transducer is provided. The method includes:

a. specifying a transmit aperture and individual element transmit characteristics for each transmit beam in a set of transmit beams used for acquiring an image frame, where the set of transmit beams includes at least one transmit beam that insonifies at least part of the desired field of view;

b. determining, through measurement or simulation, various attributes of each transmit beam in the set of transmit beams at a plurality of field points that cover the field of view;

c. storing the attributes for each field point for repeated use in processing each new image frame;

d. transmitting and receiving echo signals using the set of transmit beams and storing the echo signals in a memory;

e. processing the stored echo signals using one or more of the stored transmit beam attributes to qualify the ultrasound echo signal received from a field point contributed by a given transmit beam for use in image formation, and to specify how the signal should be processed;

f. producing and combining multiple image parameters from the set of qualified transmit beams that overlap for a field point to produce a final image parameter that constitutes a field point value for the image frame.

In accordance with a further aspect of the present disclosure, the measured or simulated attribute of a transmit beam consists of at least one of the following:

a. a peak intensity of the transmit beam over the duration of a transmit event;

b. a time that the peak intensity of the transmit beam occurred at the field point;

c. a transmit pulse duration determined by the time that the pulse intensity exceeds a threshold that is typically less the −20 dB of the pulse peak;

d. a ratio between the peak intensity and any other peaks of beam intensity that occur during a transmit event at the field point; and e. an angle of incidence of the wavefront of the transmit beam pulse with a chosen axis used to specify the location of the field point.

In one embodiment of the present disclosure, the set of transmit beams is designed to maximize frame rate by using unfocused beams to insonify the field of view with a small number of transmit/receive acquisitions. In another embodiment, the set of transmit beams is designed to maximize spatial and contrast resolution, while still acquiring frames at rates greater than in conventional scanning systems.

In accordance with another aspect of the present disclosure, the processing of received echo signals for tissue or blood velocity uses the stored angle of the incident transmit beam attribute to correct velocity calculations based on Doppler frequency shifts, obtaining magnitude and direction of motion at each field point.

BRIEF DESCRIPTION OF THE SEVERAL VIEWS OF THE DRAWINGS

The foregoing and other features and advantages of the present disclosure will be more readily appreciated as the same become better understood from the following detailed description when taken in conjunction with the accompanying drawings, wherein.

DETAILED DESCRIPTION

Figure 1:
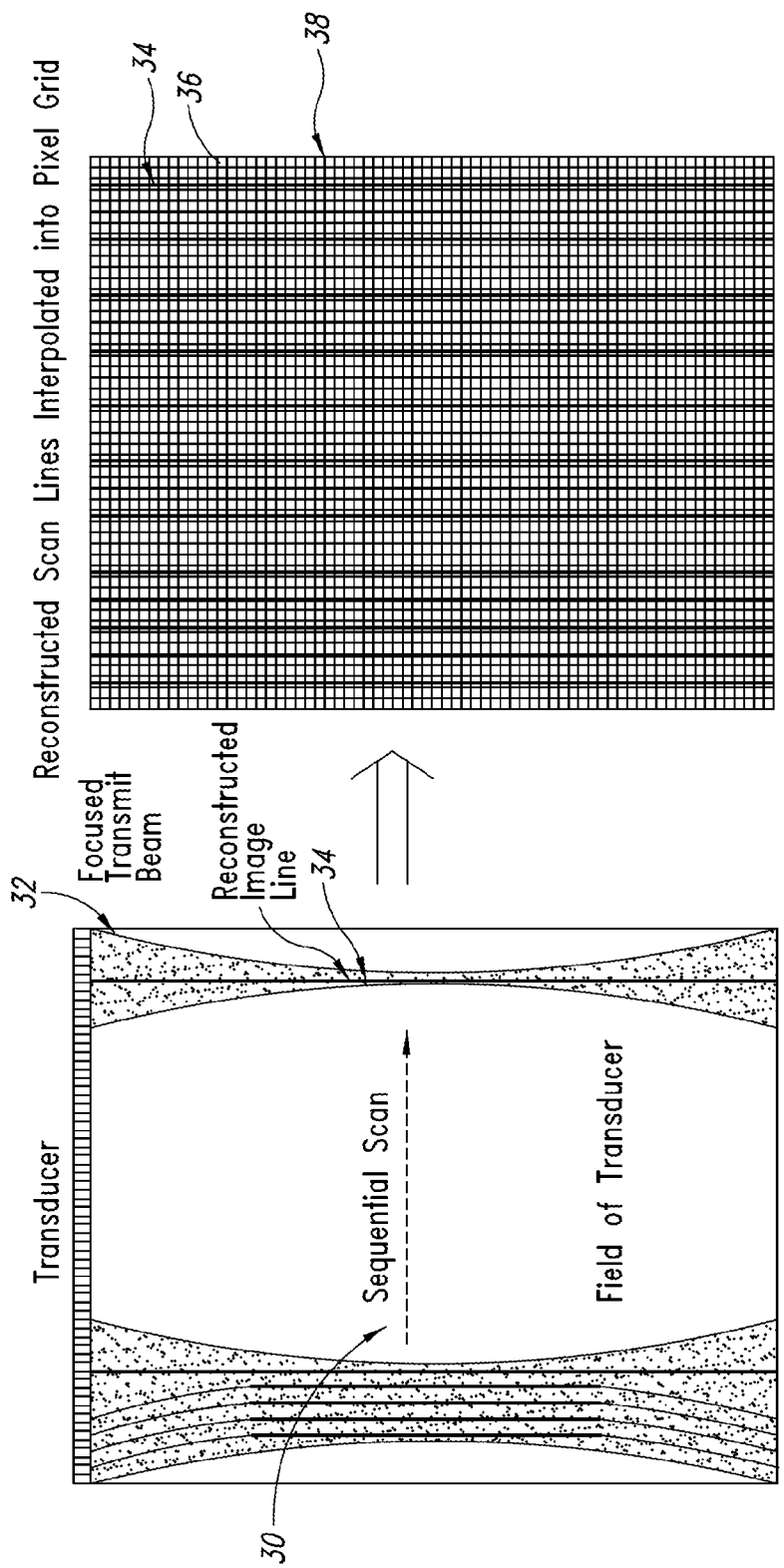
FIG. 1 is an illustration of conventional scanning and image formation using focused beams.

In the following description, certain specific details are set forth in order to provide a thorough understanding of various disclosed embodiments. However, one skilled in the relevant art will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its broadest sense, that is as meaning "and/or" unless the content clearly dictates otherwise.

The headings and Abstract of the Disclosure provided herein are for convenience only and do not interpret the scope or meaning of the embodiments.

A method of ultrasound image formation and corresponding system is described that can employ sets of partially or fully overlapping transmit beams with various beam characteristics, including transmit beams focused or weakly focused in depth, or completely unfocused, to insonify a medium. In accordance with one aspect of the present disclosure, the method involves determining in advance through simulation or measurement the relevant characteristics of the transmit beam that will be produced at each image field point as the transmit pulse for a given beam in the set passes through the field point.

Such characteristics may include the peak acoustic intensity that results at the field point, the time that the peak acoustic intensity occurs at the field point, the duration of intensity greater than a certain level (the pulse duration), the ratio between the peak intensity and any other peaks of beam intensity that occur during the transmit event at the field point, and the angle of incidence of the peak transmit intensity wave with the field point. One or more of these characteristics can then be used to qualify regions of the transmit field that are suitable for image formation. These transmit field characteristics can be stored in memory in a computing system and then recalled during image formation processing for an ultrasound scan that uses the previously characterized transmit beam set. The beam characteristics can be used to determine which field points fall into the qualified regions of a transmit beam and how the echo signals returned for a given transmit beam at each field point should be processed. The final acoustic image parameter at a field point is derived from the combination of processed signals from one or more of the transmit beams in the set.

The present disclosure provides a system and method that utilizes more of the echo signals generated from each transmit beam and combines signals from multiple overlapping transmit beams in the image formation process to improve image resolution and/or reduce frame acquisition times. As shown in FIG. 1, an individual transmit beam 32 can insonify a fairly large region of the transducer field of view. Moreover, the insonified regions in typical sequential scans overlap considerably, with the same field point being insonified by several transmit beams in the set. Instead of reconstructing image parameters only along the axis of each beam, it is possible to process other field points contained within a transmit beam, and combine the result from each overlapping beam at a field point. To carry out such a reconstruction method, we need some way of determining the insonified region of a transmit beam, and measuring parameters of the region that aid in determining the best type of processing for the field points in the region.

Figure 2:
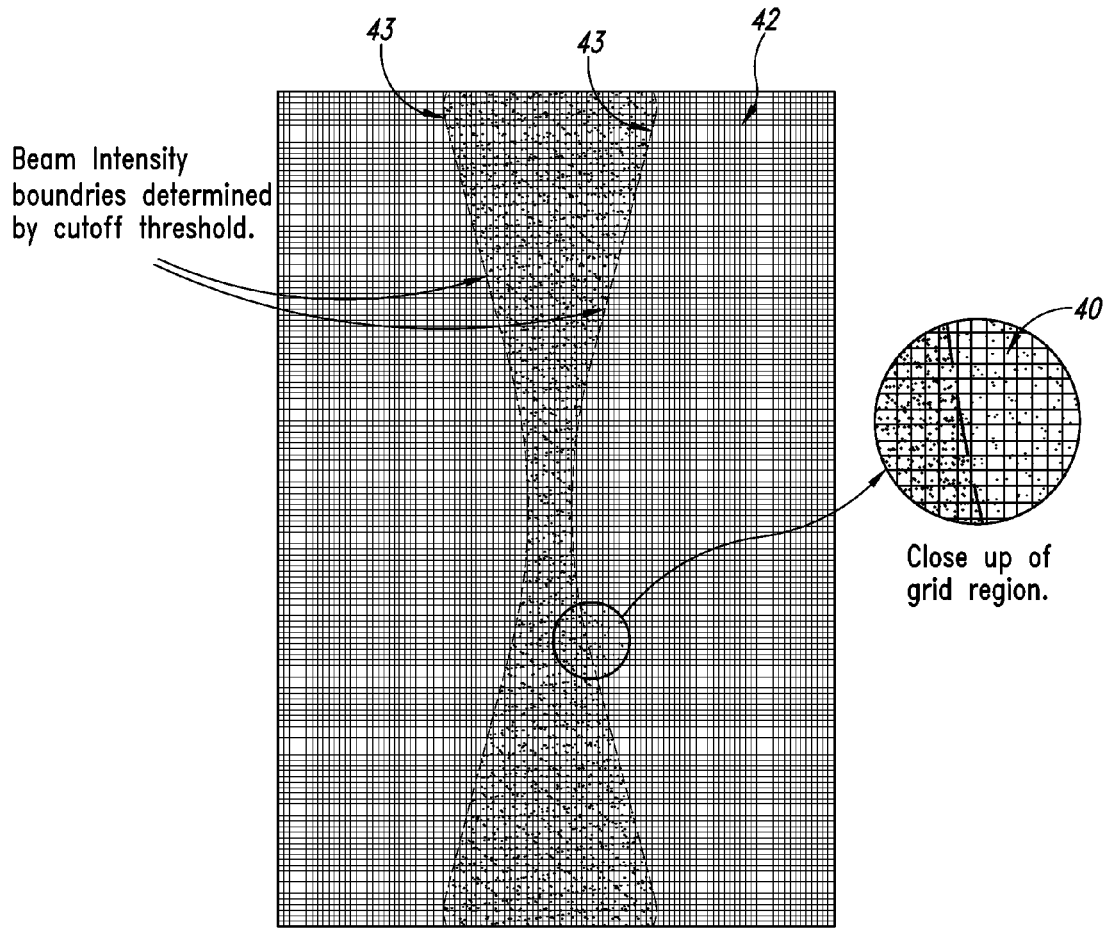
FIG. 2 is an illustration of the maximum intensities of a transmit beam on a grid of field points showing boundaries determined by a cutoff threshold.

One method of determining the extent of the region insonified by a transmit beam is to compute using beam simulation techniques or by direct measurement the maximum intensity of the transmit beam at each field point 40 in a grid 42 of field points, as shown in FIG. 2. At some known time, which depends on the speed of sound in the medium, a pulsed transmit beam will generate an intensity peak at field points in the insonified region of the beam. This intensity peak will vary with the location of the field point with respect to the axis of the beam, typically diminishing with increasing distance from the beam axis. The magnitude of the intensity peak at a field point is indicated by the shade of grey of the field point in FIG. 2. At some distance from the beam axis, the peak intensity will become weak enough that the echo signals returning from a field point will become undetectable or unusable, as they will blend with background noise and acoustic clutter. A cutoff threshold can therefore be established at some ratio of the largest peak intensity, for which field points with intensities below the threshold are designated to be outside the insonified region of the transmit beam. One may choose to have different cutoff thresholds at different field points, since the overall intensity of the transmit pulse at a field point can vary with depth, tissue attenuation, and other factors. The various thresholds then define the boundaries 43 of the main insonified region of the beam, which we will also refer to as the qualified region (see FIG. 2). For field points within the insonified region of the transmit beam, we can also use the peak intensity values to normalize the echoes returning from each field point in image formation operations. This can provide a uniform intensity reconstruction of image parameters over the main insonified region of the transmit beam.

Figure 3:
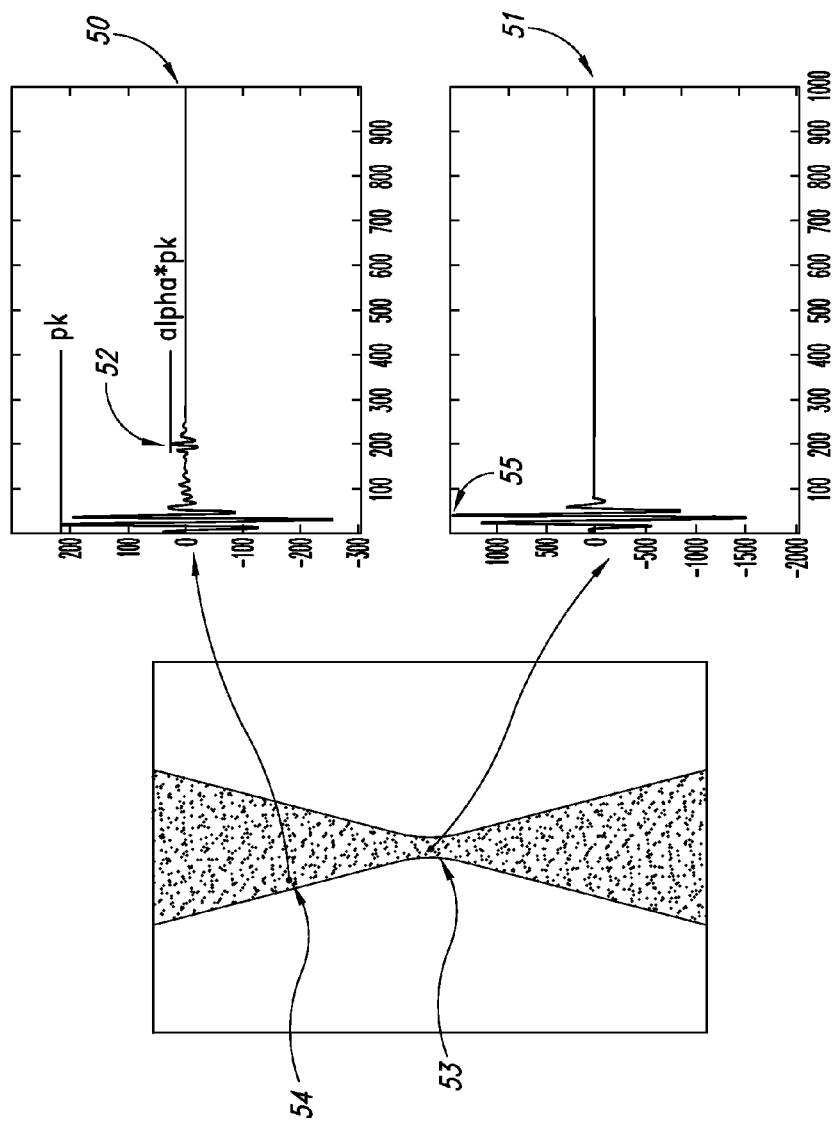
FIG. 3 is an illustration of a transmit waveform at different field points.

Other transmit beam characteristics than the peak intensity of the transmit pulse can be important for qualifying which field points can be used for image formation. For field points at distances removed from the focal point of the beam, the time duration of the transmit pulse may be extended, since the arrival times for transmit pulses from the individual elements in the transducer are not coincident. If one looks at the time duration of the pulse intensity at a field point 53 on the axis of the beam at the focal point, compared with the duration of the pulse intensity at a field point 54 off axis and away from the focal point, one might see waveforms 50 and 51, as shown in FIG. 3.

The intensity waveform 51 for the field point at the focal point is well behaved and forms a singular peak, 55. The intensity waveform 50 at the off axis point is more spread out, and has a secondary peak 52. The spreading of the central peak and the presence of secondary peaks in the intensity waveform at a field point can lead to degraded resolution and increased clutter in the processing of echo signals for image formation from the field point. It is therefore useful to exclude field points where the central peak of the intensity waveform has spread by more than a specified amount or where there are secondary peaks higher than some specified ratio of the central peak. In FIG. 3, the secondary peak is a ratio alpha of the main peak, and we can set a maximum value of alpha that can be used to reject field points with high secondary peaks. A desirable value of alpha for insuring a low contribution of secondary peaks would be less than 0.1 (−20 dB).

Using some or all of the above mentioned characteristics of the transmit beam to qualify which field points can be used for image formation with that particular beam, we can then be assured that the image parameters computed for a field point are accurate and not compromised by unwanted signals. Therefore, for each transmit beam in our set it is possible to perform image formation operations over field points covering a substantial region of the transmit beam, rather than only along the beam axis. This allows designing a set of transmit beams that cover the desired image field of interest with only a few partially or fully overlapping transmit beams, rather than the large number of beams required when only the beam axis is reconstructed. The use of fewer than 64 beams allows reduced acquisition times and higher frame rates. In addition, since the same field point can be a qualified field point for multiple transmit beams in a set, the image formation processing can utilize echo signals from more than just one transmit beam.

Figure 4:
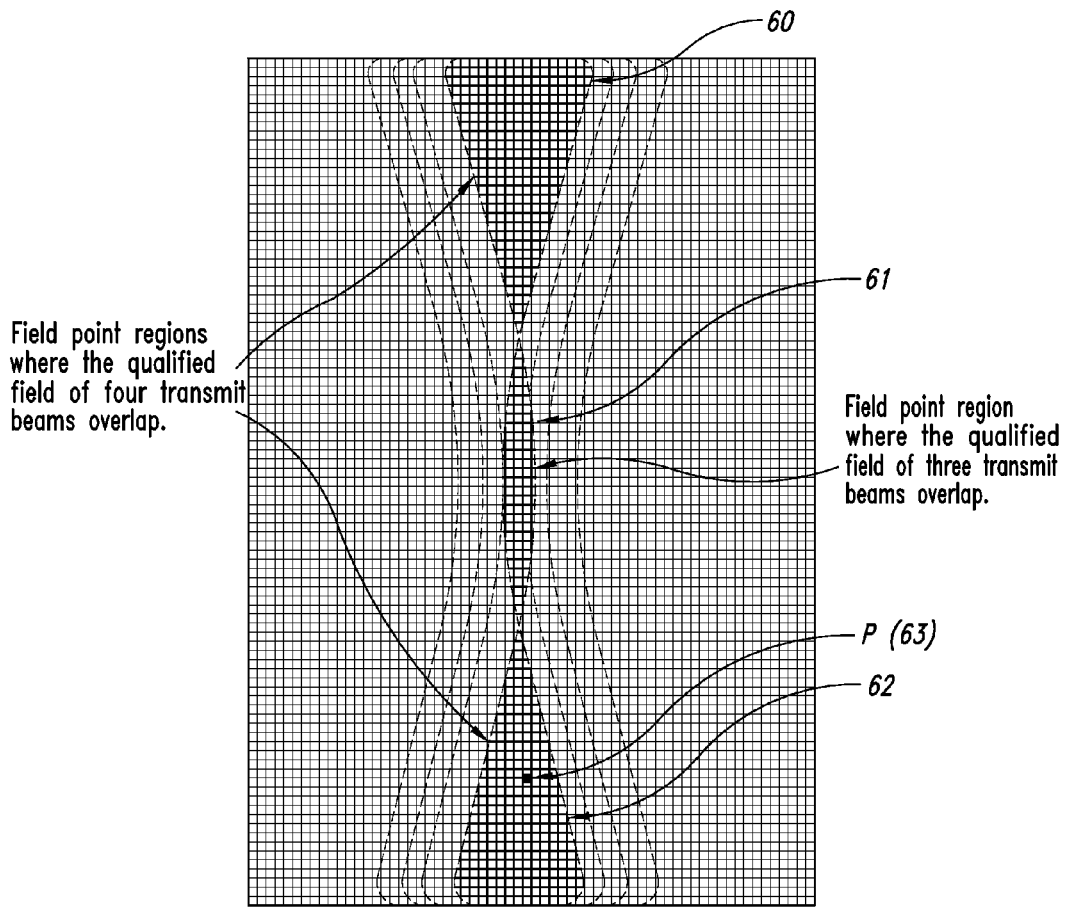
FIG. 4 is an illustration of four overlapping transmit beams showing field points in overlapped regions where three or four received echo signals can be combined for image formation.

For a specific example, consider a given field point, P (63), that is insonified by a set of multiple transmit beams, $T_{1-N}$, as shown in FIG. 4. In FIG. 4, three regions 60, 61, 62 are shown containing field points with four overlapping beams, three overlapping beams and four overlapping beams, respectively. As is described more fully, image formation using multiple overlapping transmit beam regions can provide enhanced spatial resolution. For each transmit beam, the following characteristics are determined at the field point, P, by simulation or direct measurement.

$I(T_n)$—Peak acoustic intensity at P.

$tp(T_n)$—Time from the start of transmit to the occurrence of the peak acoustic intensity at P.

$tb(T_n)$—Time duration of acoustic intensity greater than some specified fraction of $tp(T_n)$.

$r(T_n)$—Ratio of the intensity of any secondary intensity peaks to $I(T_n)$.

$\theta(T_n)$—Angle of incidence of acoustic wave front with respect to axis of transducer.

For echo image formation, a complex signal value, Sn, can be obtained for the field point P, for each transmit beam in the set, by delaying and summing individual transducer element receive signals to reconstruct the echo signal generated by any reflector at the field point. This is the well known method of beamforming, although in this case, signal reconstruction is being performed at a specific field point, rather than points located along the axis of each transmit beam. For purpose of computing the time delays for the various transducer element signals to use in the signal reconstruction, the time from the start of transmit to the occurrence of the peak acoustic intensity at the filed point, tp(Tn), can be used.

In this example case, we might have as many as eight transmit beams that produce some acoustic energy at our field point, P, and we could calculate eight complex signal values, $S_{1-8}$. To obtain an overall complex signal value at P for the set of transmit beams, we can combined the individual signal values as follows:

$$S_P = (S_1*N_1 + S_2*N_2 + S_3*N_3 + S_4*N_4 + S_5*N_5 + S_6*N_6 + S_7*N_7 + S_8*N_8)/8$$

where $N_{1-8}$ are normalization constants, obtained by computing the inverse of the peak acoustic intensity values, $I(T_{1-8})$. For example, if the intensity at P of transmit beam $T_1$ is 0.5 (in some arbitrary unit) and the intensity at P of transmit beam $T_4$ is 1.0, we would compute $N_1=2$ and $N_4=1$. In this case, we would expect signal value $S_1$ to be half the intensity of signal value $S_4$, so the signal value $S_1$ would be multiplied by 2, to give it an equal contribution to the overall sum as signal value $S_4$.

The above combining equation does not take into account several factors. The peak acoustic intensity, $I(T_n)$, for a particular transmit beam may be so weak that if would only add noise to the combined signals. To prevent this, we set the normalization constant, $N_n$, to zero for $S_n$ where $I(T_n)$ is less than a specified threshold, such as 0.05 times the maximum acoustic intensity at P. In addition, the time duration of the transmit pulse at point P, $tb(T_n)$ may become extended for certain transmit beams, $T_n$, where the field point P is not located along the beam axis. Using the signals from these transmit beams would degrade image resolution, and so we set the normalization constants for these beams to zero if the value of $tb(T_n)$ is greater than a specified amount, such as 1.2 times the shortest transmit pulse duration. Finally, for certain transmit beams, the transmit pulse at P may have developed undesirable characteristics, such as secondary peaks that occur later in time from the primary peak. In this case, we can use the ratio of intensity of secondary peaks, $r(T_n)$, to qualify these beams. If the value of $r(T_n)$ is above a certain threshold, such as 0.02 (the secondary peak is greater than 2% of the intensity of the primary peak), the normalization constant can be set to zero. With these added constraints, our combining formula might be modified as follows:

When qualified by an intensity threshold applied to $I(T_n)$:

$$S_P=(\cancel{S_1 {}^* N_1}+S_2{}^*N_2+S_3{}^*N_3+S_4{}^*N_4+S_5{}^*N_5+S_6{}^*N_6+S_7{}^*N_7+\cancel{S_8{}^*N_8})/6$$

When further qualified by a duration threshold, $tb(T_n)$ and/or a ratio of secondary peaks, $r(T_n)$:

$$S_P=(\cancel{S_2{}^*N_2}+S_3{}^*N_3+S_4{}^*N_4+S_5{}^*N_5+S_6{}^*N_6+\cancel{S_7{}^*N_7})/4$$

Our combined complex signal for P is now based on four of the eight beams that contribute, but our criteria for selection has allowed only beams with sufficient intensity and well formed transmit pulses to contribute. The qualified transmit beam regions are shown in FIG. 4, along the regions where the qualified regions overlap. The resulting combined signal at P will typically provide a more accurate estimate of the echo return from the field point compared with the signal from a single beam. The complex signal value, $S_P$, can then be further processed to obtain acoustic image parameters such as echo intensity, or phase information for Doppler velocity measurements.

The collection of acoustic image parameters at the various field points in the transducer field of view then compose an image frame. The frame can then be processed in the computing system for display on a display device, printing out on a printer, transmission to other computing systems, and the like. The method extracts additional acoustic information at the various field points from the multiple transmit beams that insonify each field point, providing advantages over conventional beamforming methods: Improved image quality can be obtained with an equal or fewer number of beams than used in conventional processing, or ultrasound image frames can be formed with fewer transmit beams without loss of image quality, thus providing higher acquisition frame rates.

Instead of using fewer transmit beams to cover the field of interest at higher frame rates, we can also use larger sets of transmit beams with smaller intensity fields. With smaller intensity fields, a transmit beam produces fewer echoes from the entire transducer field of view, including fewer echoes from large off-axis specular surfaces that can contribute to increased clutter in image formation. Transmit beams with smaller intensity fields can still have overlapping qualified image formation regions, retaining the benefit of enhanced spatial resolution. With the lower levels of clutter, an enhancement in contrast resolution is also obtained.

To combine the signals for a field point from multiple transmit beams, we need to know the precise time of arrival of the transmit pulse wavefront for each transmit beam. Knowing this time and the time for the echoes generated at the field point to travel back to the individual array elements allows us to combine the individual element signals in a phase coherent manner to reconstruct the signal from the field point. The time of arrival of the transmit pulse at a field point for a given transmit beam can be determined by simulation or by actual measurement, similar to the peak intensity and peak intensity duration. The time of arrival of a transmit pulse for each qualified field point of a transmit beam can then be predetermined and stored in a memory device, for use during the image formation processing of the echo signals produced by the transmit beam. During image formation, the time of arrival of the pulse is added to the time of travel from the field point to a particular transducer element to determine the point in time of the element's received echo signal to use for combining its signal with the signals obtained from other transmit beams.

Combining the echo signals for a field point insonified by multiple overlapping transmit beams can improve image spatial and contrast resolution at the field point. This is due to the fact that each beam may have a slightly different angle of incidence on the field point, and this results in a form of synthetic transmit focusing that mimics the geometric focusing of a transmit beam at a focal point. Combining the signals from overlapping transmit beams therefore can have the effect of extending the depth of field where the image is focused, providing the same result as the combining of multiple transmit focal depths, but without having to transmit multiple times at each beam location along the scan. This allows improved image resolution without having to extend frame acquisition times.

In addition, the combination of multiple transmit beams in image formation can improve contrast resolution. Contrast resolution is improved through reduction of clutter and speckle artifacts. Clutter is due to echoes from targets other than those at the field point that arrive at the receiving elements at the same time as those from the field point. The echoes come from other sources and are often produced by side lobes or grating lobes of the transmit beam.

By combining the echo signals from transmit beams with different origins and angles of incidence at the field point, the clutter signals at the field point are varied, and tend to combine incoherently. The echoes from the field point combine coherently, and adding the signals from multiple beams can therefore increase the signal-to-clutter ratio. The speckle pattern in ultrasound images is also partly dependent on the transmit beam characteristics, and the combining of signals from multiple beams will tend to average out these variations as well.

Image formation with a set of overlapping transmit beams can be quite complex to implement, and is preferably performed using software, pixel-oriented processing, which is described more fully below. The field points can be at the pixel locations of an image display, or at the pixel locations of a virtual image, which will eventually be interpolated into a high resolution display. At each field point, one must determine the number of overlapping qualified transmit beam regions whose received echo signals can be used for image formation. Since each transmit beam in the set can produce a different intensity at a given field point, the returned signals should be normalized to correct for these intensity differences before combining. The combining process should also keep track of and normalize the number of transducer elements that participate in the receive process for each transmit beam, as this will also affect signal strength. These normalization factors are independent for each field point in the image field of interest, and must be either computed in real time as the image formation processing proceeds, or kept in a storage table where the parameters can be retrieved during the processing of each image frame.

When the image formation processing is aimed at measuring motion in the image field of interest, the use of a set of overlapping, qualified transmit beam regions has some unique advantages. Since we can compute through beam simulation or direct measurement the angle of incidence of the transmit pulse wavefront with each field point, we can know the magnitude of the Doppler frequency shift that would be returned from any motion vector at the field point. The different transmit beams in the overlapping set can be designed to generate different angles of incidence at each field point, and from the change in the measured motion vector component with each angle of incidence, we can compute the absolute magnitude and direction of the motion vector. This then provides much more accurate blood velocity and tissue motion sensing than conventional motion imaging techniques that use a single transmit beam angle of incidence.

Conventional Doppler imaging utilizes multiple transmit and receive signal acquisitions for each transmit beam position in a scan, generating an ensemble of received signals at each position that can be used to detect motion along the beam axis. The conventional approach measures the component of the velocity vector along the axis of the beam, rather than the absolute velocity. If the transmit beams used in the conventional Doppler imaging method are sufficiently broad so that they provide some overlap at the field points of interest, the same scanning sequence can provide absolute velocity information. Each ensemble of acquisitions at a transmit beam location allows measuring a single component of the motion vector at each field point, along with the previously determined angle of incidence of the transmit beam. The next ensemble of acquisitions at the next transmit beam location provides an additional component of the motion vector at field points that overlap with the previous beam. Then by combining the multiple components obtained from multiple overlapping transmit beams at each field point along with the known transmit beam angles of incidence, one can compute the absolute magnitude and direction of the motion vector.

In the above discussion, we have not specified explicitly the geometry of the set of overlapping transmit beams for a given use. This is because the design of the set of overlapping beams will be dependent both on the ultrasound application and the desired image formation parameter to be measured. Typically, a transmit beam is shaped by controlling the size of the transmit aperture, the weighting or apodization of the transmitting elements contained in the aperture, and the time delay to the start of each transmitting element's waveform. The waveforms of the individual transmitters can also be controlled in most systems.

The general rules for designing a set of transmit beams for enhanced image formation are as follows: a) If there is little or no motion in the image field of interest and a minimal number bright specular reflectors, design a set of beams which are broad and have substantial overlap, so that each field point is touched by greater than 5 beams. Soften the transmit beam focus through apodization or use a very deep focal point to achieve sufficient overlap at the narrowest portions of the beam. In addition, design the set of transmit beams to provide different angles of incidence of the transmit pulse wavefront at the majority of field points. b) If there is substantial motion in the field of interest and/or large specular reflectors, design a set of relatively narrow transmit beams with a small amount of overlap at regions where motion is expected, reducing the number of overlapped beams at field points in the region to two or three beams. This will minimize errors in coherent image formation with multiple beams due to media motion.

The principle advantage of the above image formation method is that it allows the ultrasound image engineer to optimize the imaging performance of the system for different imaging applications and measurements. One can have very high frame rates (greater than 100 frames per second), using only a few transmit beams per frame, yet still obtain reasonable image quality, or typical frame rates (around 30 frames per second) with larger numbers of beams, providing the best image spatial and contrast resolution. For Doppler imaging, the magnitude and direction of blood flow or tissue motion can be obtained without sacrificing frame rate.

Pixel Oriented Processing

Figure 5:
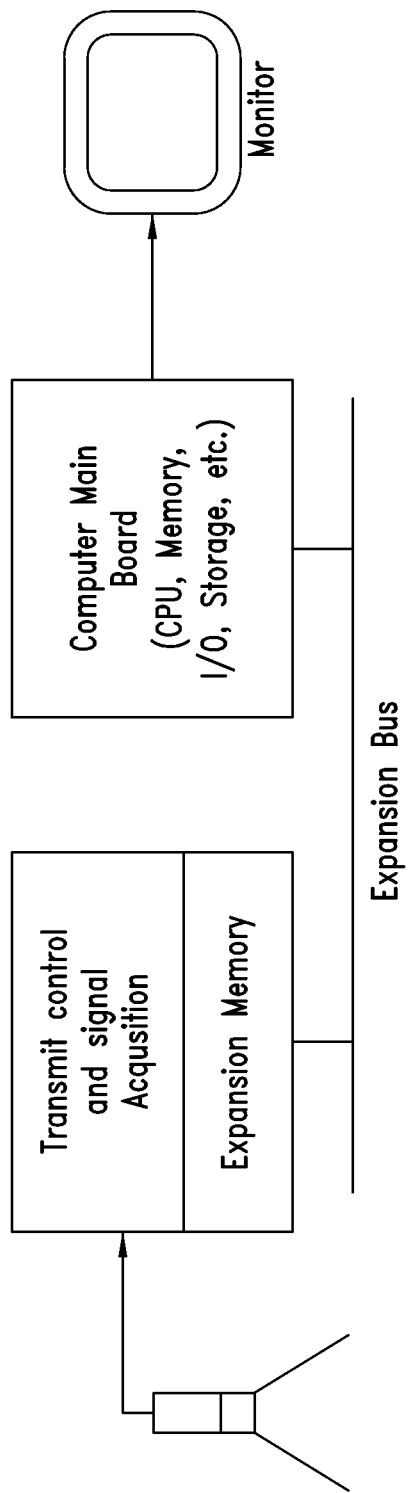
FIG. 5 is a schematic representation of a software-based architecture of one embodiment of pixel-oriented processing.

The foregoing method can be implemented in a computing system that utilizes a software-based method and system architecture in accordance with one embodiment of the present disclosure. The system implements all real-time processing functions in software. The proposed architecture is shown schematically in FIG. 5.

The only custom hardware component in the software-based system is an acquisition module that connects to the expansion bus of the computer that contains the pulse generation and signal acquisition circuitry, and a large block of expansion memory that is used to store signal data. The signal acquisition process consists of amplifying and digitizing the signals returned from each of the transducer elements following a transmit pulse. Typically, the only filtering of the signals prior to digitization, other than the natural band-pass filtering provided by the transducer itself, is low pass, anti-aliasing filtering for A/D conversion. The signals are sampled at a constant rate consistent with the ultrasound frequencies involved, and the digitized data are stored in memory with minimal signal processing. The straight-forward design of the signal acquisition allows the circuitry to be implemented with off-the-shelf components in a relatively small amount of board area.

Figure 6:
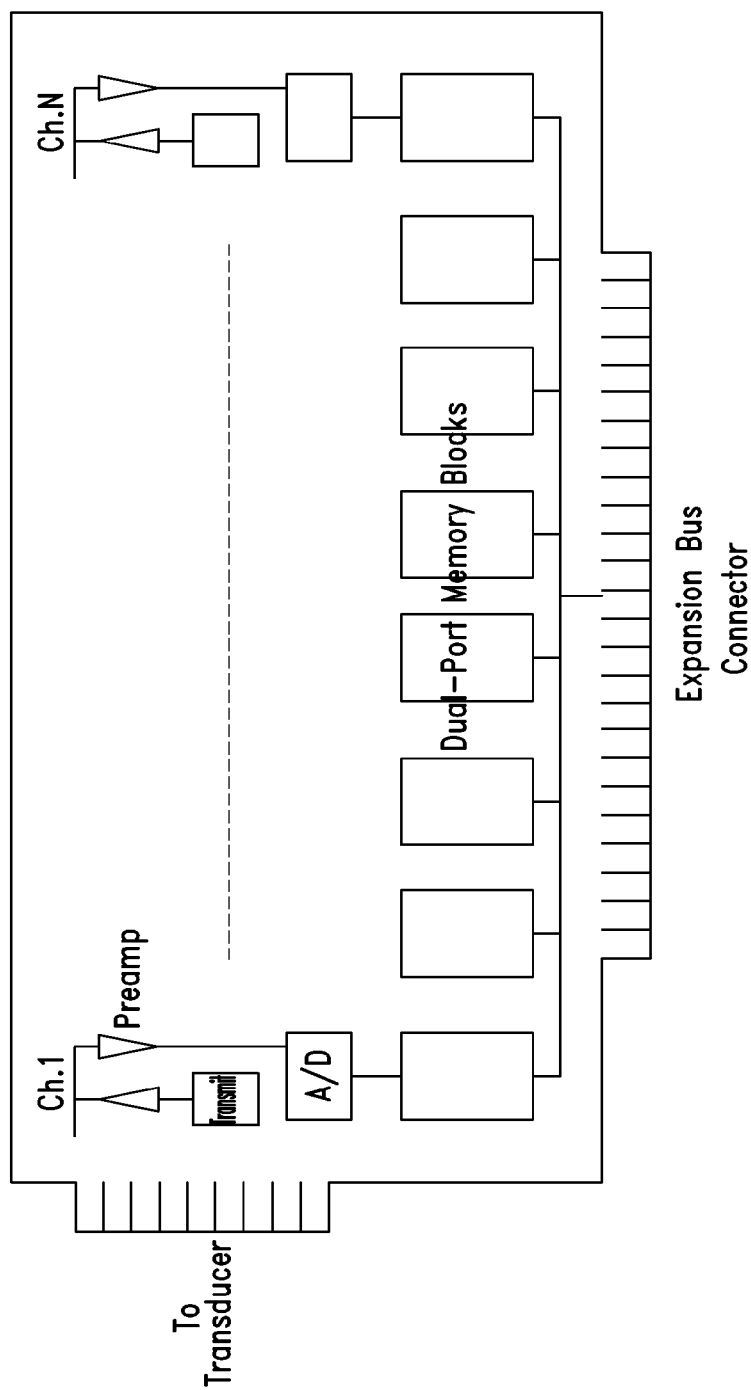
FIG. 6 is a diagram of a plug-in module formed in accordance with the pixel-oriented processing.

A more detailed look at the acquisition module is shown in FIG. 6. Multiple acquisition channels are shown, each composed of a transmitter, receiver pre-amplifier, A/D converter, and memory block. During receive, the transducer signals are digitized and written directly to the individual memory blocks. The memory blocks are dual-ported, meaning they can be read from the computer side at the same time acquisition data is being written from the A/D converter side. The memory blocks appear as normal expansion memory to the system CPU(s). It should be noted that the size of the acquisition module is not limited to the normal size of a standard computer expansion card, since the system is preferably housed in a custom enclosure. Also, multiple acquisition modules can be used to accommodate a large number of transducer elements, with each module processing a subset of the transducer aperture.

The components for the acquisition module, including amplifiers, A/D converters and associated interface circuitry, and the needed components for transmit pulse generation and signal acquisition are readily commercially available components and will not be described in detail herein. The memory block needed for RF data storage of echo signals obtained from received echoes is essentially the same circuitry as found in commercially available expansion memory cards, with the addition of a second direct memory access port for writing the digitized signal data. (The received echo signal data is generally referred to as RF data, since it consists of high frequency electrical oscillations generated by the transducer.)

The memory can be mapped into the central processor's address space and accessed in a manner similar to other CPU memory located on the computer motherboard. Alternately, the RF data can be transferred from the acquisition module to the host computer by mean of direct memory access. The size of the memory on the acquisition module is such that it can accommodate the individual channel receive data for up to 256 or more separate transmit/receive cycles. Since the maximum practical depth of penetration for round trip travel of an ultrasound pulse in the body is about 500 wavelengths, a typical sampling rate of four times the center frequency will require storage of as many as 4000 samples from an individual transducer element. For a sampling accuracy of 16 bits and 128 transducer channels, a maximum depth receive data acquisition will require approximately one megabyte of storage for each transmit/receive event. To store 256 events will therefore require 256 MB of storage, and all totaled, a 128 channel system could be built on as few as one or two acquisition modules.

Another aspect of the software-based ultrasound system is the computer motherboard and its associated components. The motherboard for the proposed design should preferably support a multi-processor CPU configuration, for obtaining the needed processing power. A complete multi-processor computer system, complete with power supply, memory, hard disk storage, DVD/CD-RW drive, and monitor is well-known to those skilled in the art, can be readily commercially purchased, and will not be described in greater detail.

A software-based ultrasound system must truly achieve "high-performance," meaning image quality comparable to existing high-end systems, in order to provide a significant benefit to the health care industry. This level of performance cannot be achieved by simply converting the flow-through processing methods of current systems to software implementations, since a simple addition of all the processing operations needed for one second of real-time imaging in the flow-through architecture gives a number that exceeds the typical number of operations per second currently achievable with several general purpose processors. Consequently, new processing methods are required that achieve a much greater efficiency than the flow-through methods.

In one embodiment of the software-based ultrasound system architecture of the present invention, the input data for signal and image processing consists of the set of RF samples acquired from individual transducer channels following one or more transmit events.

Figure 7:
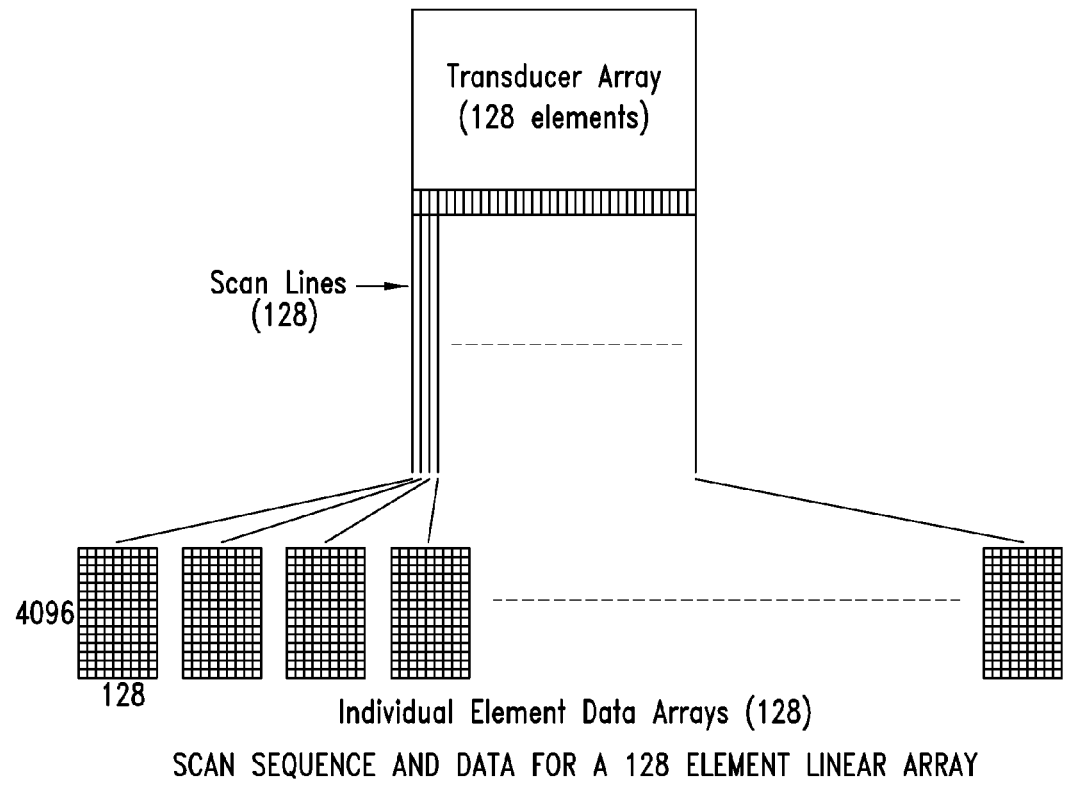
FIG. 7 is a schematic representation of the acquisition data for a 128 element linear array formed in accordance with the pixel-oriented processing.

For an example, let us consider a typical 2D imaging scanning mode with a 128 element linear transducer array, as shown in FIG. 7.

In this case, a 'transmit event' would consist of timed pulses from multiple transducer elements to generate a plurality of acoustic waves that combine in the media to form a focused ultrasound beam that emanates outwards from an origin point on the transducer at a specific element location. Multiple transmit events (128 in all) produce ultrasound beams that are sequentially emitted incrementally across the width of the transducer face, thus interrogating an entire image frame. For each of these transmit beams, the received echo data are collected from each of the 128 receiver elements in the transducer and organized into a data array with each column representing the sampled echo signal received by the corresponding transducer element. Thus, each array has 128 columns, corresponding to the 128 transducer elements, and a number of rows corresponding to the number of samples in depth that were taken (in this case, we will assume 4096 rows resulting in 4096 samples). These 128 data arrays then constitute an RF data set that is sufficient to produce one complete image frame.

It is worth noting that in the flow-through architecture, the RF data set described above does not even exist (at least not all at one time), since the beam and image formation takes place as the data streams in from the transducer. In other words, as the data return to each element after a transmit event, they are processed and combined (referred to as beam forming) to generate a single RF signal representing the focused return along a single beam (scan line). This RF signal is processed (again in real-time) into echo amplitude samples, which are stored in a memory array. When all beam directions have been processed, the echo amplitude data are then interpolated and formatted into a pixel image for display. Since all processing takes place in real-time, the processing circuitry must be able to 'keep up' with the data streaming in from the transducer elements.

In the software-based architecture of the present invention, all input data is stored prior to processing. This uncouples the acquisition rate from the processing rate, allowing the processing time to be longer than the acquisition time, if needed. This is a distinct advantage in high frequency scans, where the depth of acquisition is short and the sample rate high. For example, a 10 MHz scan head might have a useable depth of imaging of around four centimeters. In this case, the speed of sound in tissue dictates that each of the 128 transmit/receive events acquire and store their data in 52 microseconds, a very high acquisition data rate. In the flow-through architecture, these acquisition data would be formed into scan lines in real-time at high processing rates. In the software-based architecture of the present invention, the storage of RF data allows the processing to take as long as the frame period of the display, which for real-time visualization of tissue movement is typically 33 milliseconds (30 frames/second). For 128 pixel columns (the rough analogy to scan lines), this would allow 258 microseconds of processing time per column, rather than the 52 microseconds of the flow-through architecture. This storage strategy has the effect of substantially lowering the maximum rate of processing compared with the flow-through architecture for typical scan depths.

The storing of input data reduces the maximum processing rates but doesn't necessarily reduce the number of processing steps. To accomplish this, a new approach to ultrasound data processing is taken. The first step is to recognize that the ultimate goal of the system when in an imaging mode is to produce an image on the output display. An ultrasound image has a fundamental resolution that depends on the physical parameters of the acquisition system, such as the frequency and array dimensions, and can be represented as a rectangular array of pixel values that encode echo amplitude or some other tissue (acoustic) property. The density of this rectangular pixel array must provide adequate spatial sampling of the image resolution. It is recognized that display images need not consist only of rectangular arrays of pixels, but could consist of any arbitrary set of pixels, representing different geometric shapes.

The next step is to start with one of the pixels in this image array and consider which sample points in the RF data set contribute to the calculation of this pixel's intensity, and determine the most efficient way of accessing and processing them. This approach is a completely different approach than the one utilized by the current flow-through architecture because only information that contributes to pixels on the display needs to be processed. In the approach of the present invention, a small region on the display image will take less overall processing time than a large image region, because the small region contains fewer pixels. In contrast, the flow-through processing methods must be designed to handle the maximum data stream bandwidths, independent of the image region size.

After processing the pixel array required to adequately represent the ultrasound image, the array can be rendered to the computer display at an appropriate size for viewing. The graphics processor of the computer, requiring no additional CPU processing, can typically carry out this operation, which consists of simple scaling and interpolation.

We next consider the processing strategy for a single pixel of our ultrasound image. In this discussion, we will assume that our objective is to obtain the echo intensity at the corresponding spatial location of the pixel with respect to the transducer array. Other acoustic parameters may be similarly obtained. Our first step is to find the region of acquisition RF data containing samples that contribute to the echo intensity calculation. To accomplish this for the scanning method of FIG. 7, we first find the acquisition scan line that comes closest to intersecting the pixel location, and then use the corresponding individual element data array.

Figure 8:
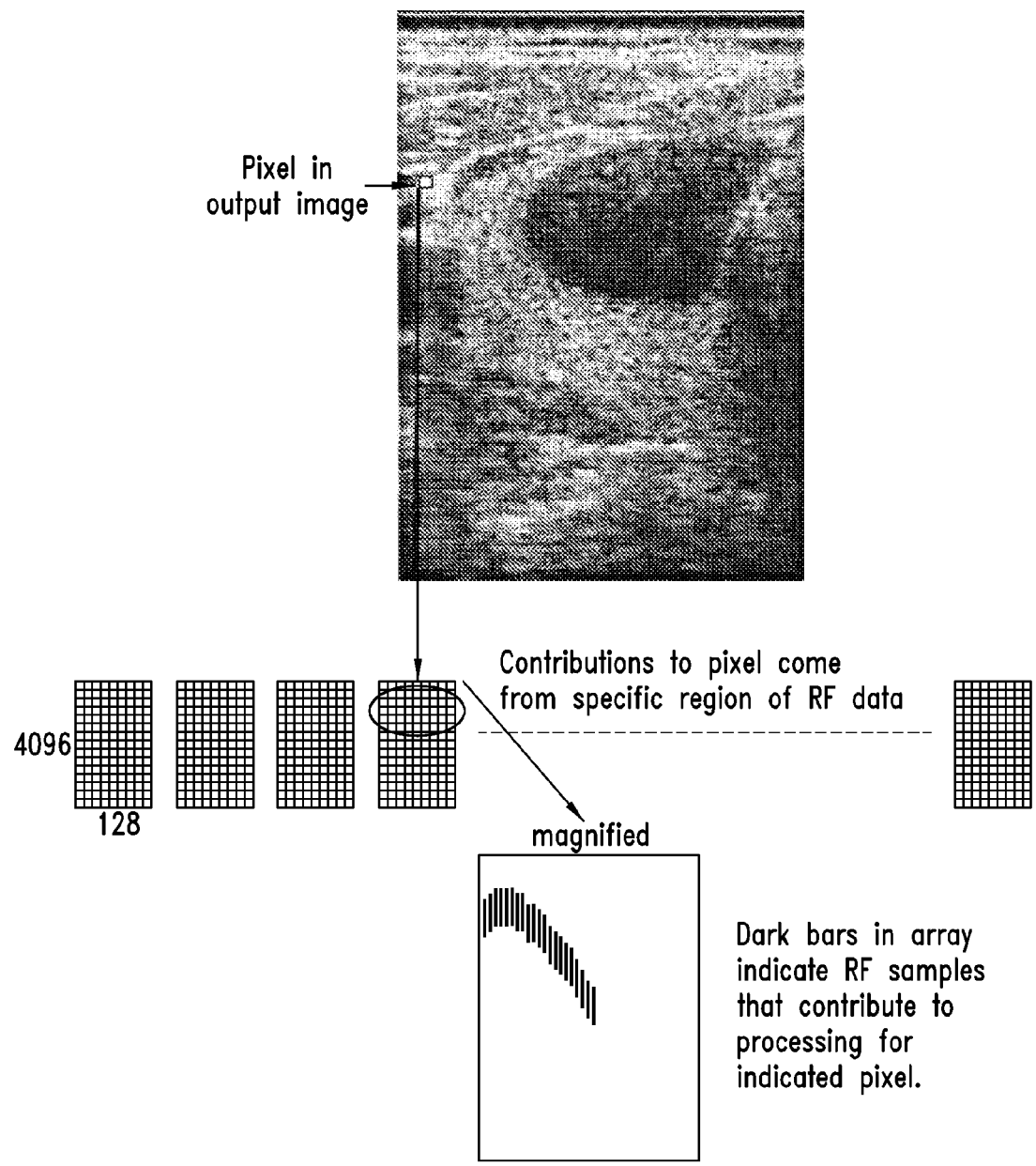
FIG. 8 is an illustration of a pixel mapping process used in pixel-oriented processing.

FIG. 8 shows this mapping process for an example pixel in an ultrasound image. In FIG. 8, the indicated pixel maps to the closest acquisition line of the scan, which in this case is scan line 4, whose RF data resides in the fourth individual element RF data array (which represents data collected from the fourth transmit/receive event). More than one RF data array could be chosen as contributing to the pixel signal, but for this example we will consider only a single data array.

Out next step is to map out the region in the individual element array containing samples that contribute to the pixel's intensity calculation. This mapping process is fairly complex and depends on several factors. The transducer elements each have a region of sensitivity that determines how they will respond to a signal returning from a particular point in the image field. For a given image point, only elements that have sensitivities above a predetermined threshold need be considered, since if the sensitivity is too low, an element will not contribute useful information to the pixel's quantity. This sensitivity threshold then determines the number of element data columns to include in the mapped region.

The starting depth of the mapped data region is determined by the arrival time of the returning echo at each individual transducer element. As shown in FIG. 8, the image point signal for elements further away from the image point is captured later in time, and so the starting point of the data set is deeper in memory. Finally, the depth range needed for the mapped data region is dependent on the duration of the transmit pulse generated. Longer transmit pulses will excite the image point for a longer period of time, generating echo signals that extend over a larger depth span of the RF memory.

Fortunately, many of the factors that go into determining the region of mapped data can be pre-computed for a given pixel grid, since this grid does not change over the multiple frames of a real-time image sequence. Using pre-computed factors, the mapped data region for a given pixel can be rapidly and efficiently determined, saving considerable computations during real-time imaging.

After selecting out the pixel mapped RF data, we can organize it into a matrix, $RFP_{nm}$, as shown below.

The notation '$P_{nm}$' refers to the image pixel in row n, column m. The matrix columns are the vertical bars of FIG. 11 where it is assumed that $$RFP_{nm} = \begin{bmatrix} a_{11} a_{12} \ldots a_{1k} \\ a_{21} \\ \ldots \\ \ldots \\ a_{j1} \ldots a_{jk} \end{bmatrix}$$

the number of samples, j, in each vertical bar are the same. The number of samples, j, is dependent on the range of RF data in time needed for capturing the signal generated by the transmit pulse. The index, k, is the number of channels in the RF data array that have adequate signal strength from to the image point to participate in the intensity calculation. The process of computing the signal intensity value of pixel $P_{nm}$ now consists of a series of matrix operations that eventually lead to a single value.

Figure 9:
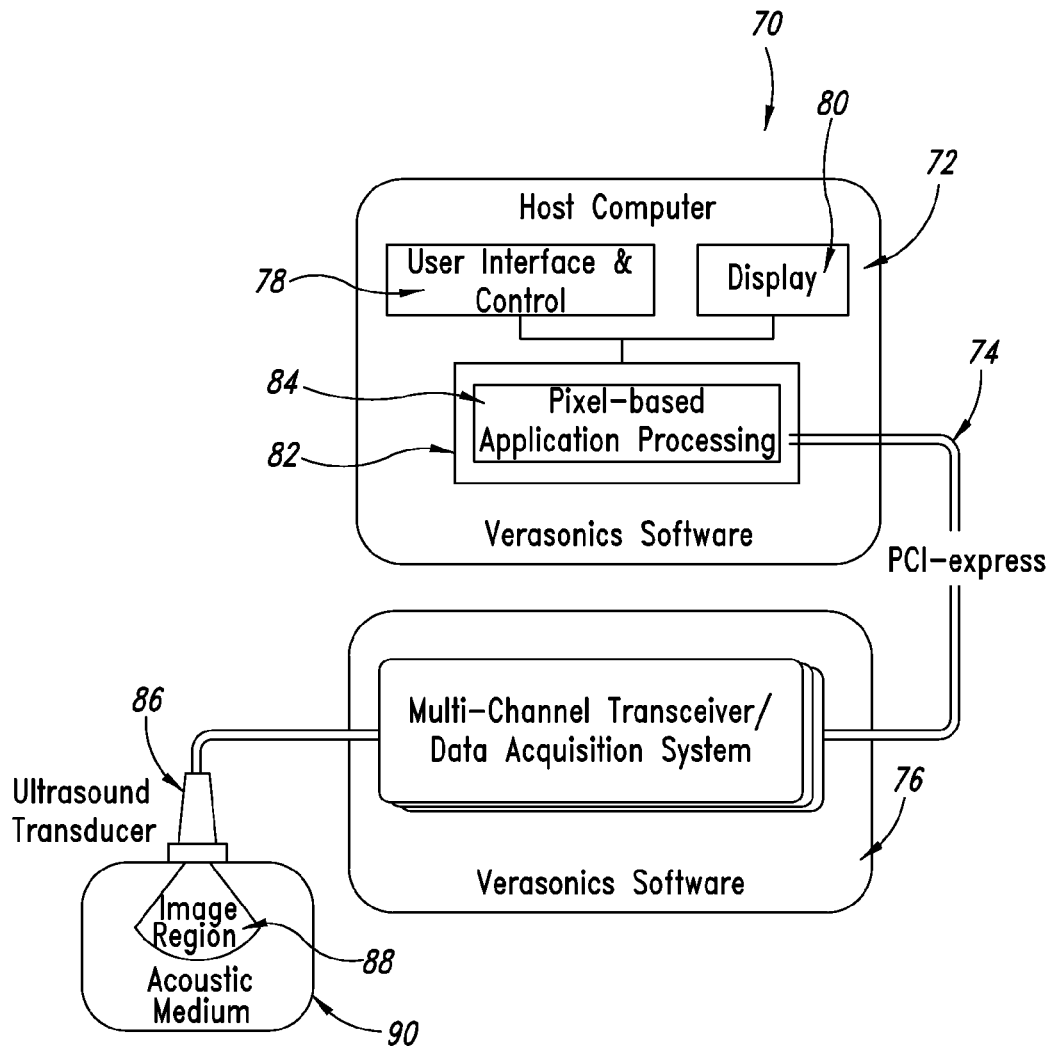
FIG. 9 illustrates a high-level representation of the system architecture for the processes of the present disclosure.

FIG. 9 is a high-level representation of the system architecture adaptable for implementing the processes of the present disclosure, while FIG. 10 is a schematic representation of a software-based architecture of one embodiment. In addition FIG. 11 is a diagram of a plug-in module formed in accordance with the pixel-oriented processing described above.

More particularly, FIG. 9 shows a system level block diagram that represents a high-level system architecture 70 for implementing the processes of the present disclosure. It is to be understood that this is merely one representative embodiment, and the illustrated architecture 70 is not a requirement for all embodiments of the present disclosure.

The architecture 70 includes a host computer 72 coupled via a PCI-express 74 to a multi-channel transceiver and data acquisition system 76. The host computer 72 has a user interface and control 78, and a display 80, both coupled to a processor 82 that utilizes the pixel-based application processing software 84. The multi-channel transceiver and data acquisition system 76 hardware are coupled to an ultrasound transducer 86 that is used to image a region 88 in an acoustic medium 90 for display on the display 80, such as a monitor, projector, or for transmission to another device for display or operation of the device or both. Because these components are readily commercially available, they will not be described in detail herein.

Using pixel oriented processing allows for complex echo signal reconstructions of the type mentioned previously that utilize overlapping transmit beams. In this method, a look-up-table memory is used to store the computed or measured beam characteristics of each transmit beam in a set of transmit beams at each of a grid of points that are positioned with respect to the field of view of the transducer. Pixel oriented signal reconstruction is performed at each point in the grid of points, where the echo signal contributions of each transmit beam are computed and combined, using the look-up-table parameters corresponding to the reconstruction point.

The various embodiments described above can be combined to provide further embodiments. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method of improving the resolution and frame rate of ultrasound image frames obtained from a field of view covered by a plurality of field points in a medium using a multi-element transducer, comprising:
   a. transmitting a set of beams into the medium, each transmit beam in the set of transmit beams having a transmit aperture and individual element transmit attributes used for acquiring an image frame, where the set of transmit beams includes at least one transmit beam that insonifies at least part of the field of view in the medium;
   b. determining, through measurement or simulation, a plurality of attributes of each transmit beam in the set of transmit beams at the plurality of field points that cover the field of view;
   c. storing the plurality of attributes for each field point of the plurality of field points for repeated use in processing each new image frame;
   d. transmitting and receiving echo signals using the set of transmit beams and storing the echo signals in a memory;
   e. processing the stored echo signals using one or more of the stored transmit beam attributes to qualify the ultrasound echo signal received from a field point contributed by a given transmit beam for use in image formation, and to specify how the signal should be processed; and
   f. producing and combining multiple image parameters from the set of qualified transmit beams that overlap for a field point to produce a final image parameter that constitutes a field point value for the image frame.

2. The method of claim 1, where the determining the measured or simulated plurality of attributes of the transmit beam at a field point comprises determining at least one of the following attributes:
   a. a peak intensity of the transmit beam over the duration of a transmit event;
   b. a time that the peak intensity of the transmit beam occurred at the field point;
   c. a transmit pulse duration determined by the time that the pulse intensity exceeds a threshold that is typically less the −20 dB of the pulse peak;
   d. a ratio between the peak intensity and any other peaks of beam intensity that occur during a transmit event at the field point; and
   e. an angle of incidence of a wavefront of the transmit beam pulse with a chosen axis used to specify the location of the field point.

3. The method of claim 1, wherein the processing of the stored echo signals includes compensating a gain of each stored echo signal by using a peak transmit intensity of each transmit beam at the field point.

4. The method of claim 1, comprising arranging the field points in a rectangular array at corresponding locations of pixels in an image frame to be displayed.

5. The method of claim 1, comprising forming the set of transmit beams to maximize frame rate by using unfocused transmit beams to insonify the field of view with less than 64 transmit/receive acquisitions.

6. The method of claim 1, comprising forming the set of transmit beams to provide optimal spatial and contrast resolution by controlling the amount of overlap of the transmit beams in the set.

7. The method of claim 1, where the processing of the stored echo signals comprises processing the stored echo signals to extract velocity information for tissue or blood motion in the medium using a stored angle of an incident transmit beam attribute to obtain correct velocity calculations based on Doppler frequency shifts in order to obtain magnitude and direction of motion at each field point.

8. A system implemented in a computer for improving the resolution and frame rate of ultrasound images from a field of view covered by field points in a medium obtained from a multi-element transducer, comprising:
   a processor and a memory configured to perform the following:
   a. specifying a transmit aperture and individual element transmit attributes for each transmit beam in a set of transmit beams used for acquiring an image frame, where the set of transmit beams includes at least one transmit beam that insonifies at least part of the field of view in the medium;
   b. determining, through measurement or simulation, plurality attributes of each transmit beam in the set of transmit beams at a plurality of field points that cover the field of view;
   c. storing the attributes for each field point for repeated use in processing each new image frame;
   d. transmitting and receiving echo signals using the set of transmit beams and storing the echo signals in a memory;
   e. processing the stored echo signals using one or more of the stored transmit beam attributes to qualify the ultrasound echo signal received from a field point contributed by a given transmit beam for use in image formation, and to specify how the signal should be processed; and
   f. producing and combining multiple image parameters from the set of qualified transmit beams that overlap for a field point to produce a final image parameter that constitutes a field point value for the image frame.

9. The system of claim 8, where the measured or simulated attributes of the transmit beam comprises at least one of the following:
   a. a peak intensity of the transmit beam over the duration of a transmit event;
   b. a time that the peak intensity of the transmit beam occurred at the field point;
   c. a transmit pulse duration determined by the time that the pulse intensity exceeds a threshold that is typically less the −20 dB of the pulse peak;
   d. a ratio between the peak intensity and any other peaks of beam intensity that occur during a transmit event at the field point; and
   e. an angle of incidence of a wavefront of the transmit beam pulse with a chosen axis used to specify the location of the field point.

10. The system of claim 8, where the processing of the stored echo signals includes compensating a gain of each stored echo signal by using a peak transmit intensity of each transmit beam at the field point.

11. The system of claim 8, where the field points are arranged in a rectangular array at corresponding locations of pixels in an image frame to be displayed.

12. The system of claim 8, where the set of transmit beams are configured to maximize frame rate by using unfocused transmit beams to insonify the field of view with less than 64 transmit/receive acquisitions.

13. The system of claim 8, where the set of transmit beams is configured to provide optimal spatial and contrast resolution by controlling the amount of overlap of the transmit beams in the set.

14. The system of claim 8, where the processing of the stored echo signals comprises processing of the stored echo signals to extract velocity information for tissue or blood motion in the medium using a stored angle of an incident transmit beam attribute to obtain correct velocity calculations based on Doppler frequency shifts in order to obtain magnitude and direction of motion at each field point.

15. A method of improving the resolution and frame rate of ultrasound image frames obtained from a multi-element transducer, comprising:
   a. specifying a transmit aperture and individual element transmit characteristics for each transmit beam in a set of transmit beams used to acquire an image frame, where the set of transmit beams includes at least one transmit beam that insonifies at least part of a desired field of view;
   b. determining, through measurement or simulation, a plurality of attributes of each transmit beam in the set of transmit beams at a plurality of field points that cover the field of view;
   c. storing the plurality of attributes for each field point for repeated use in processing each new image frame;
   d. transmitting and receiving echo signals using the set of transmit beams and storing the echo signals in a memory;
   e. processing the stored echo signals using one or more of the stored transmit beam attributes to qualify the ultrasound echo signal received from a field point contributed by a given transmit beam for use in image formation, and to specify how the signal should be processed, the processing of the stored echo signals including processing the stored echo signals to extract velocity information for tissue or blood motion using a stored angle of an incident transmit beam attribute to obtain corrected velocity calculations based on Doppler frequency shifts in order to obtain magnitude and direction of motion at each field point; and
   f. producing and combining multiple image parameters from the set of qualified transmit beams that overlap for a field point to produce a final image parameter that constitutes a field point value for the image frame.

16. The method of claim 15, where the determining the measured or simulated plurality of attributes of the transmit beam at a field point comprises determining at least one of the following attributes:
   a. a peak intensity of the transmit beam over the duration of a transmit event;
   b. a time that the peak intensity of the transmit beam occurred at the field point;
   c. a transmit pulse duration determined by the time that the pulse intensity exceeds a threshold that is typically less the −20 dB of the pulse peak;
   d. a ratio between the peak intensity and any other peaks of beam intensity that occur during a transmit event at the field point; and
   e. an angle of incidence of a wavefront of the transmit beam pulse with a chosen axis used to specify the location of the field point.

17. The method of claim 15, wherein the processing of the stored echo signals includes compensating a gain of each stored echo signal by using a peak transmit intensity of each transmit beam at the field point.

18. The method of claim 15, comprising arranging the field points in a rectangular array at corresponding locations of pixels in an image frame to be displayed.

19. The method of claim 15, comprising forming the set of transmit beams to maximize frame rate by using unfocused transmit beams to insonify the field of view with less than 64 transmit/receive acquisitions.

20. The method of claim 15, comprising forming the set of transmit beams to provide optimal spatial and contrast resolution by controlling the amount of overlap of the transmit beams in the set.

21. A system implemented in a computer for improving the resolution and frame rate of ultrasound images obtained from a multi-element transducer, comprising:
   a processor and a memory configured to perform the following:
      a. specifying a transmit aperture and individual element transmit characteristics for each transmit beam in a set of transmit beams used for acquiring an image frame, where the set of transmit beams includes at least one transmit beam that insonifies at least part of a desired field of view;
      b. determining, through measurement or simulation, various attributes of each transmit beam in the set of transmit beams at a plurality of field points that cover the field of view;
      c. storing the attributes for each field point for repeated use in processing each new image frame;
      d. transmitting and receiving echo signals using the set of transmit beams and storing the echo signals in a memory;
      e. processing the stored echo signals using one or more of the stored transmit beam attributes to qualify the ultrasound echo signal received from a field point contributed by a given transmit beam for use in image formation, and to specify how the signal should be processed, the processing of the stored echo signals includes processing the stored echo signals to extract velocity information for tissue or blood motion using a stored angle of an incident transmit beam attribute to obtain correct velocity calculations based on Doppler frequency shifts in order to obtain magnitude and direction of motion at each field point; and
      f. producing and combining multiple image parameters from the set of qualified transmit beams that overlap for a field point to produce a final image parameter that constitutes a field point value for the image frame.

22. The system of claim 21, where the measured or simulated attributes of the transmit beam comprises at least one of the following:
   a. a peak intensity of the transmit beam over the duration of a transmit event;
   b. a time that the peak intensity of the transmit beam occurred at the field point;
   c. a transmit pulse duration determined by the time that the pulse intensity exceeds a threshold that is typically less the −20 dB of the pulse peak;
   d. a ratio between the peak intensity and any other peaks of beam intensity that occur during a transmit event at the field point; and
   e. an angle of incidence of a wavefront of the transmit beam pulse with a chosen axis used to specify the location of the field point.

23. The system of claim 21, where the processing of the stored echo signals includes compensating a gain of each stored echo signal by using a peak transmit intensity of each transmit beam at the field point.

24. The system of claim 21, where the field points are arranged in a rectangular array at corresponding locations of pixels in an image frame to be displayed.

25. The system of claim 21, where the set of transmit beams are configured to maximize frame rate by using unfocused transmit beams to insonify the field of view with less than 64 transmit/receive acquisitions.

26. The system of claim 21, where the set of transmit beams is configured to provide optimal spatial and contrast resolution by controlling the amount of overlap of the transmit beams in the set.

* * * * *